United States Patent [19]

Truelock et al.

[11] 4,382,446

[45] May 10, 1983

[54] HEAT TRANSFER DEVICES FOR THE SCALP

[75] Inventors: Donald E. Truelock, Moberly, Mo.; Richard W. Turner, Alpine, Calif.

[73] Assignee: Kay Laboratories, Inc., San Diego, Calif.

[21] Appl. No.: 199,738

[22] Filed: Oct. 23, 1980

[51] Int. Cl.³ .............................................. A61F 7/00
[52] U.S. Cl. ................................. 128/402; 128/403; 150/2.3
[58] Field of Search ............... 128/380, 399, 402, 403; 2/171.2; 150/2.3

[56] References Cited

U.S. PATENT DOCUMENTS

| | | | |
|---|---|---|---|
| 1,569,877 | 1/1926 | Owens | 150/2.3 |
| 1,964,655 | 6/1934 | Williamson | 128/380 |
| 3,149,943 | 9/1964 | Amador | 128/402 |
| 4,055,188 | 10/1977 | Pelton | 128/402 |
| 4,204,543 | 5/1980 | Henderson | 128/402 |

*Primary Examiner*—Lee S. Cohen
*Attorney, Agent, or Firm*—Thomas M. Scofield

[57] ABSTRACT

Improvements in heat exchanging head pieces for cooling or heating the entire hair bearing (scalp) area of the human head; improvements in a blank form for such product and purposes for filling with heat exchanging materials; a heat exchanging head piece for cancer chemotherapy patients to cool the scalp to prevent hair loss during chemotherapy injections; devices and processes for heat exchanging the human scalp including variable headband constriction and limitedly variable whole upper skull compression for full, holiday free cooling or heating.

37 Claims, 21 Drawing Figures

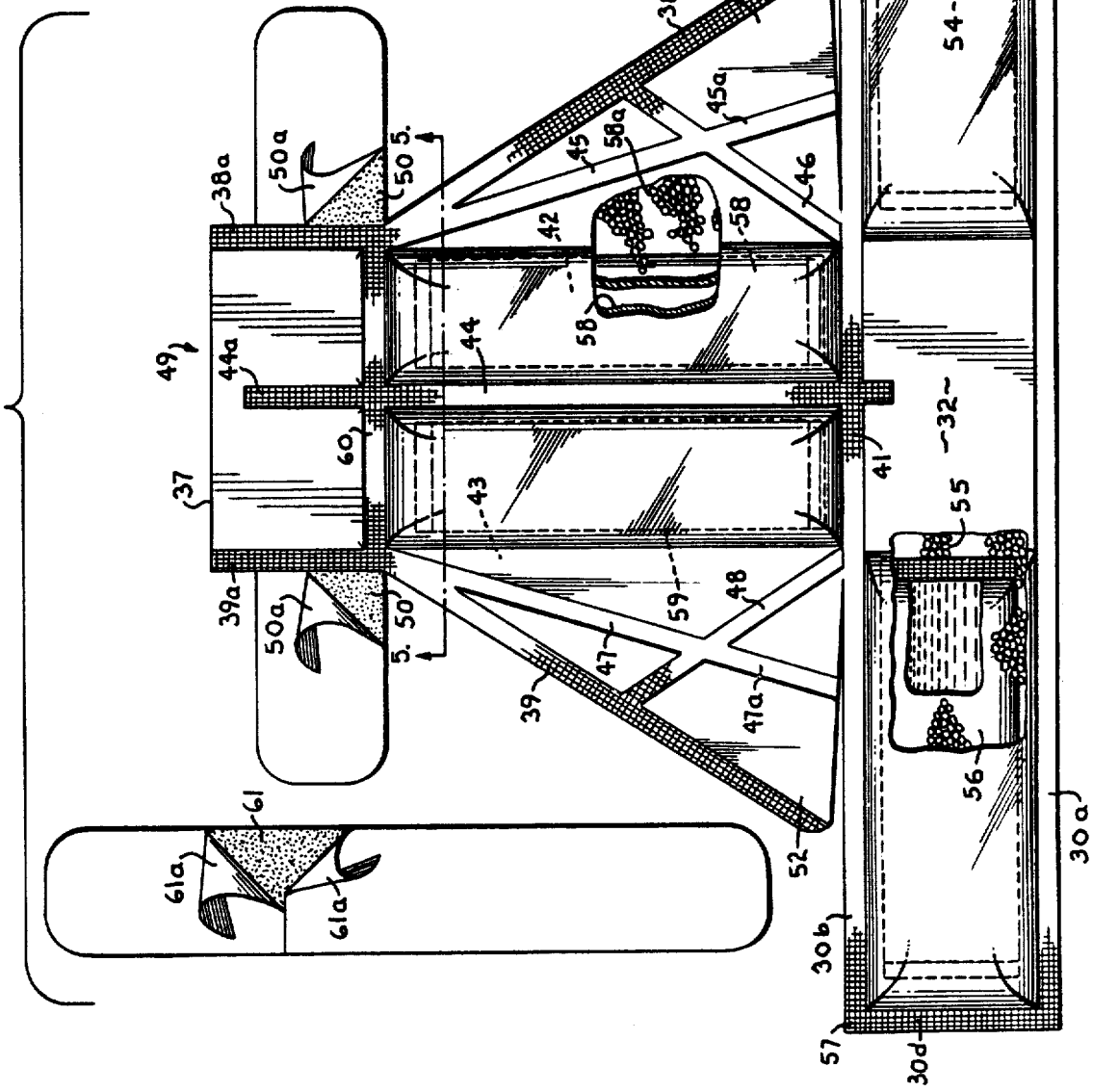

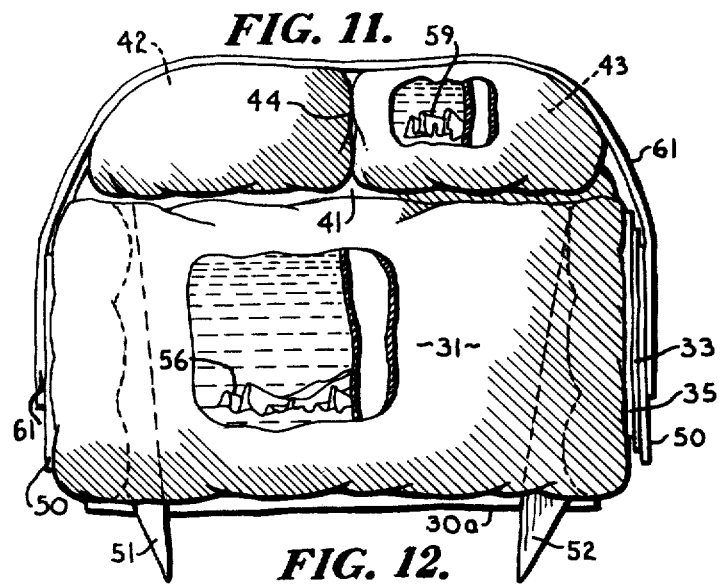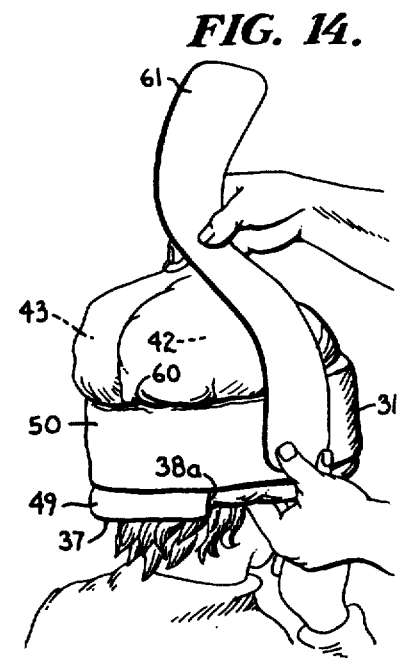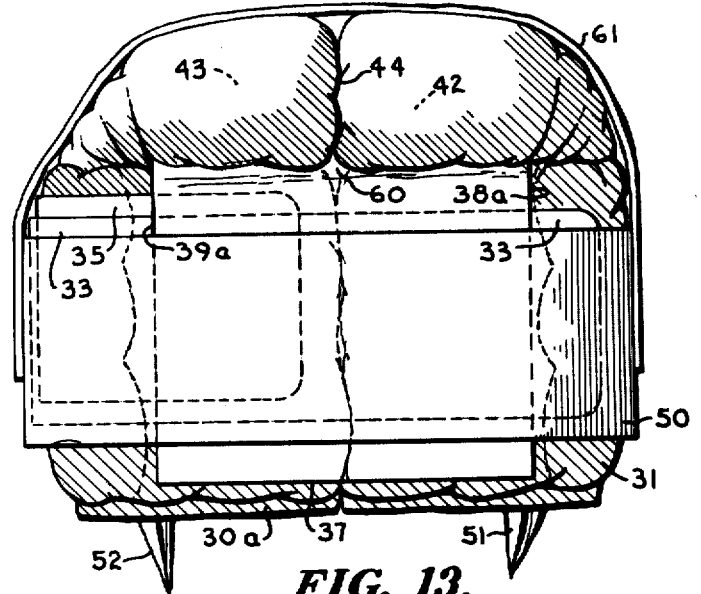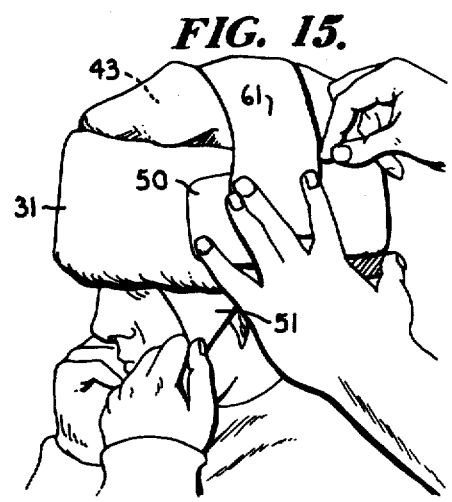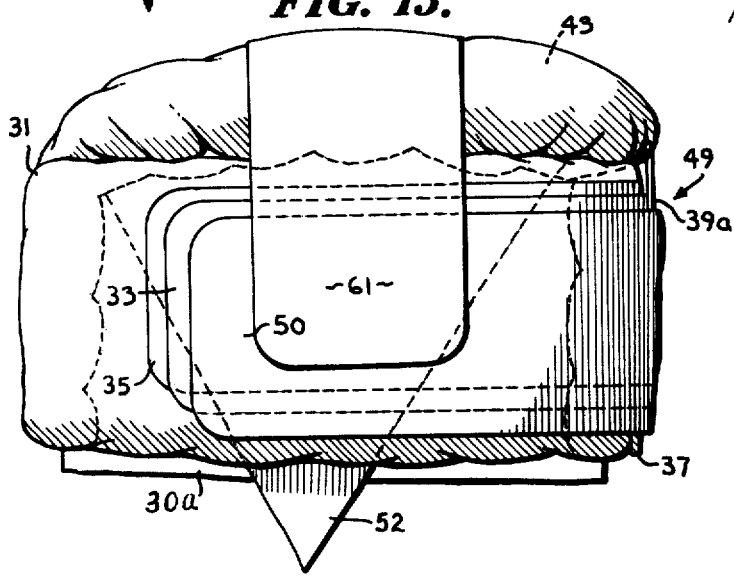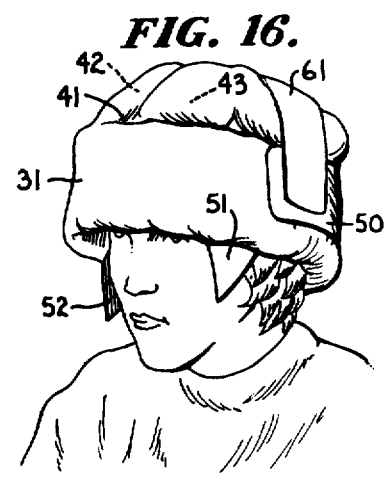

HEAT TRANSFER DEVICES FOR THE SCALP

BRIEF DESCRIPTION OF THE INVENTION

One purpose of the subject device is to (in its primary application) chill the entire hair bearing area of the scalp before, during and after a chemotherapy injection in order to minimize the quantity of chemicals that reaches the hair roots or follicles. This is accomplished by three actions enabled by the particular and unique construction of the subject device:

(1) Mild constriction around the head at the forehead-temple-rear skull base level by the headband portion of the device;

(2) Chilling of all blood rising into the scalp area by cold transmitted through the headband portion per se circumferentially of the head; and (3) Essential whole-scalp cold contact by the three (one in the headband and two in the crown portion) cells of heat exchanging material.

The subject device must not only provide mild construction and cooling heat exchange, but also must last for approximately an hour. First, in optimum procedure, the entire device is activated and applied to the head of the chemotherapy subject some 15 minutes before the chemotherapy injection. Thus, the entire scalp is cooled and circulation into the scalp, as well as therein, is impeded by blood vessel contraction (artery-vein-capillary) before treatment. The total course of a typical injection is 30 minutes. The device will remain on the patient's head continuously during the injection, as well as the noted 15 minutes therebefore. Thereafter, following the injection, the device optimally remains on the patient's head for 15 minutes. The chemotherapy chemical is presumably metabolized, deactivated or absorbed at the end of this time.

It is well known to employ the use of a constrictive band around a patient's head in chemotherapy to impede circulation to minimize hair loss. This serious impedence of circulation required by the use of a band alone is not only painful, comprising severe treatment, but potentially dangerous to the patient due to vessel compression and severe circulation restriction. The subject combination of cooling and mild constriction by the headband is, at the very least, equally effective to this drastic treatment and, in most cases far superior in effect without the stress and problems of the band alone.

The concept of cooling the scalp of a chemotherapy patient to retain hair during actual chemotherapy is not novel, per se. Ice pack applications have been proved effective. Applicants are also aware of the use of a multicellular helmet-like cap having (typically) four segments useable for the same purposes as the subject device. The latter employs two sides, one top and one rear segment. It also is know to employ refrigerable (non-freezing, moldable) liquids (familiar from prior art freezer coldpacks used for various purposes) in the place of endothermic reaction materials.

Deficiencies in the prior art devices which are cured by the subject invention include absolute removal or prevention of "holidays" in the scalp heat exchanging device at any seams thereof. Yet further, new in a scalp heat exchanging device, there is mild constriction, totally independent of the crown heat exchange of the head, around the forehead-temple-skull base zone. Full cooling of not only the entire noted headband constriction zone is provided, but, additionally, a continuous compressive contact of heat exchanging cold over the entire upper head. Finally, by using ammonium nitrate and water for cooling heat exchange, one hazard of devices employing rerefrigerable substances is avoided, specifically, freezer chilling to an excessively low temperature and frostbite encountered with such type of cold pack.

While the subject device can be readily manufactured (and repeatedly reused) employing refrigerable chemicals in all cells thereof, this is not preferred, for a number of reasons. In the first place, as noted, there is a frostbite problem requiring careful control of freezer chilling. Secondly, although this depends somewhat upon the circumstances, reusability is not necessarily always a virtue because of the highly personal nature of the subject treatment, possible cross infection, problems of cleaning, problems of storage and, as well, the problems of providing a refrigeration source at or adjacent the chemotherapy area.

The subject device essentially comprises the following elements (listed without limitation, including optional elements):

(1) A basic headband portion fabricated to be larger than the subject's head diameter whereas to provide an overlap wrap therearound, this being a single heat exchanging cell;

(2) A crown portion or top section comprising two skull top overlying cells running at right angles to the headband portion cell and connected to the headband at the top edge thereof in the forehead overlying portion thereof;

(3) A rear headband attachment strap on the basic headband portion connected to one end thereof and adapted to overlie and stick to the other end thereof in headband size controlling relationship;

(4) Grasping tabs on the crown portion (lateral of the crown portion two overlying heat exchanging cells) for grasping and holding by the subject as the operator applicator or helper wraps, initially, the basic headband portion around the subject's head and secures it in the desired position and degree of constriction (that is, the chemotherapy subject, if well enough, holds the top cells on the top of his/her head, oriented, by continuously grasping the lateral grasping tabs during basic attachment);

(5) A connecting flap at the rear end of the crown portion with a lateral adhesive extension which operates to overlie and be secured to the rear skull portion of the already attached headband portion. (This gives the basic fore and aft size adjustment and engagement to the headband for the front and rear ends of the crown portion.)

(6) One or more final straps which attach (stick) to one side of the headband opposite one ear, go over the crown portion, sticking and engaging thereto, and attach (stick) to the other side of the headband. (This last engagement, tying the sides of the headband portion to the sides and top of the crown portion, operates to integrate the entire assembly centrally, pulling the side edges of the heat exchanging cells down into contact and abutment with the top edge of the headband heat exchanging cell.)

Hereinafter will be disclosed and described a scalp heat exchanging device of great utility and efficiency which involves and employs:

(1) A head encircling, variably constrictable, heat exchanging headband portion;

(2) A top head overlying, contacting and heat exchanging crown portion which is adjustably connectible between the front and rear portions of the headband in fitting manner; and (3) Means for integrating and compacting the entire assembly of heat exchanging headband (also constricting) and heat exchanging crown portion so that the entire scalp zone is somewhat under pressure and compression with greatest constriction at the headband zone and continuous, no holiday, heat exchanging contact over the patient's entire scalp.

In a word, absolute maximal heat exchange is provided, with carefully controllable compression and constriction not only over the entire scalp zone but, most particularly, in the critical headband zone where basic circulation to the scalp originates and exits. Thus safety and comfort are maintained to the maximum degree yet efficiency is not in any way sacrificed.

Other applications (without limitation) include the cooling of the head in case of certain types of trauma to inhibit bleeding after initial treatment of injury, cold and/or heat application to the entire upper head zone in the case of headache or migraine, use in preparation for neurosurgery and the like. The pressure construction option in the headband may be employed or not as required. With or without the latter, complete, uniform upper entire head heat exchange may be obtained by use of the subject device.

THE PRIOR ART

Applicants are aware of the following prior art references and patents which relate to (1) the use of cold (or scalp hypothermia) in cancer chemotherapy. (2) heat exchange of the body (parts thereof), (3) means therefor and (4) head (or parts thereof) heat exchange, particularly cooling.

With respect to loss of hair in cancer chemotherapy and the prevention thereof, particularly see "Prevention Of Adriamycin-Induced Alopecia With Scalp Hypothermia", authors Judith Bean, R.N., M.S., Sydney E. Salmon, M.D. and Katherine Griffith, R.N., New England Journal Of Medicine, December 1979. This article additionally cites 13 references with respect to chemotherapy, adriamycin, hair loss in cancer chemotherapy and prevention of hair loss by scalp cooling of patients receiving adriamycin (doxorubicin).

Applicants are aware of the following patents directed to heat exchanging caps for the scalp which include the concept of cooling:

Werrick U.S. Pat. No. 770,031, issued Sept. 13, 1904 for "Hat Provided With Receptacle";

Morris U.S. Pat. No. 1,627,523, issued May 3, 1927 for "Face Mask";

Zelony U.S. Pat. No. 3,092,112 for "Therapeutic Compress" issued June 4, 1963;

Andrassy U.S. Pat. No. 3,463,161 "Temperature Maintaining Device", issued Aug. 26, 1969;

U.S. Pat. No. 4,118,946 Tubin, "Personnel Cooler", issued Oct. 10, 1978;

Zebuhr "Slurry Cooling Of Helmets", U.S. Pat. No. 4,172,495, issued Oct. 30, 1979.

The following patents are directed to localized cooling of parts of the body, sometimes including parts of the head:

Meinecke U.S. Pat. No. 919,614 "Hot Water Or Ice Bag", issued Apr. 27, 1909;

Baker U.S. Pat. No. 3,491,761 "Adjustable Ice Bag Harness", issued Jan. 27, 1970;

Morse U.S. Pat. No. 3,545,230 "Flexible Cooling Device And Use Thereof", issued Dec. 8, 1970;

Berndt U.S. Pat. No. 3,717,145, issued Feb. 20, 1973 for "Cold Pressure Bandage";

Pilotte U.S. Pat. No. 3,822,705 "Refrigerant Wrap For An Animal's Limb", issued July 9, 1974;

Lebold U.S. Pat. No. 3,809,684 issued June 17, 1975 for "Hot and Cold Pack";

Pelton U.S. Pat. No. 4,055,188 issued Oct. 25, 1977 for "Therapeutic Wrap".

The following patents are directed to heating devices for the scalp or head:

Larson U.S. Pat. No. 1,710,882 "Scalp Treating Device", issued Apr. 30, 1929;

Hyer U.S. Pat. No. 3,134,891 "Neck And Face Dry Heat Applicator", issued May 26, 1964;

Hariu U.S. Pat. No. 3,839,621, issued Oct. 1, 1974 for "Body Heating Device";

Mantell U.S. Pat. No. 3,908,568, issued Oct. 26, 1976 for "Heated Head Enclosure";

Murray U.S. Pat. No. 4,061,898 issued Dec. 6, 1977 for "Heat Cap"; and

Walter et al U.S. Pat. No. 4,147,921, issued Apr. 3, 1979 for "Heat Treating Articles".

A device for local cooling of extremities, including the head, by hypothermic spray of the area is seen in Smirnov, Ser. No. 587,577 "Device For . . . Hypothermy . . . ", issued June 28, 1971.

OBJECTS OF THE INVENTION

The basic object of the invention is to provide greatly improved means, devices and processes for the effective application of cooling to the entire hair bearing area of the human scalp to aid in prevention of hair loss during cancer chemotherapy.

Another object of the invention is to provide such means, devices and processes which supply and effect such cooling for a sufficient time, to the proper degree and without excess cooling or freezing, in a most efficient and effective manner.

A further object of the invention is to provide such means, devices and processes wherein there additionally is provided some circulation limitation into and out of the scalp area by mild constriction of this zone, or the periphery thereof (lower periphery including the forehead), the circulation limitation adjustable in degree, provided in the proper position (approximate cap or hat headband area) and further is cushioned for comfort.

Another object of the invention is to provide such means, devices and processes which may be applied to any individual's head, regardless of head size and/or shape, with reasonable ease of application requiring but a single helper, the ultimately applied device being snug and comfortable on the user's head after application and easily and readily removable therefrom after performance of the chemotherapy injection.

Another object of the invention is to provide such scalp heat exchanging devices which provide total area contact for heat exchange, specifically cooling, once applied. Such contact is without "holidays" which result in hair loss or possible hair loss if such were present. Full and continuous scalp contact is thus provided, both in the headband zone and the crown zone of the device, after application.

Another object of the invention is to provide such scalp heat exchanging means, devices and processes wherein structural means of adjustment during application are provided both in the headband and crown zone which may be readily employed to give a snug, continuous contact fit over the entire scalp area. Application first involves a headband application and fit which may include constriction of the circulation into the scalp zone. Thereafter, once that fit is effected properly, a crown zone application and fit is made. The latter completes assembly of the scalp contacting cap with a separate adjustment independent of yet connected to the headband zone in such manner that any user head size and shape or combination thereof may be readily adapted to and effectively and completely heat exchanged.

Yet another object of the invention is to provide a chemotherapy associated head cover which maximally protects against hair loss by providing a combination of (1) around-the-head constriction and (2) continuous contact scalp heat exchange (cooling) for maximum effectiveness in minimizing and preventing hair loss due to the physiological action of the drugs used in cancer therapy.

Another object of the invention is to provide such structures, devices and processes which are mass producible, uniform in structure and operation, long term storable without deterioration, sanitary in use and readily disposable after use and application.

Yet another object of the invention is to provide a segmented or cellular heat exchanging device for the entire human hair bearing scalp area wherein the safety, convenience and utility of a cellular device is present, yet wherein the the device is easily applied to the patient's head and scalp so that the seams between the cells do not and cannot act as nonexchange or "holiday" zones, there being continuous, pressurized contact with the entire head zone to be cooled or heat exchanged from the applied device.

Another object of the invention is to provide devices, constructions and processes as described wherein there is provided separated and separate headband and crown heat exchanging zones with respect to separate cellular constructions, yet wherein, when the device is assembled and applied to the head of a chemotherapy patient as an assembled cap, there is a unitary continuous body of cooled surface applied to the user's head.

Still another object is to provide means and methods as described for heating or cooling (depending on the chemicals employed in a one-shot device or the heat exchange applied to the device before use in a reusable device) the entire upper head zone of a person in new and efficient ways.

Other and further objects of the invention will appear in the following description thereof.

THE DRAWINGS

In the drawings, which form a part of the instant specification and are to be read in conjunction therewith, an embodiment of the invention is shown and, in the various views, like numerals are employed to indicate like parts.

FIG. 1 is a top plan view of the empty blank for the subject human scalp heat exchanger before the cells of the blank are filled with the heat exchange materials before activation (water bags and ammonium nitrate in the case of cooling). An additional required flap for assembly of the device is seen to the right side of the blank in the view included in the bracket. This figure shows the outside surface of the device (when assembled and in use).

Figures 1, 2, 3:
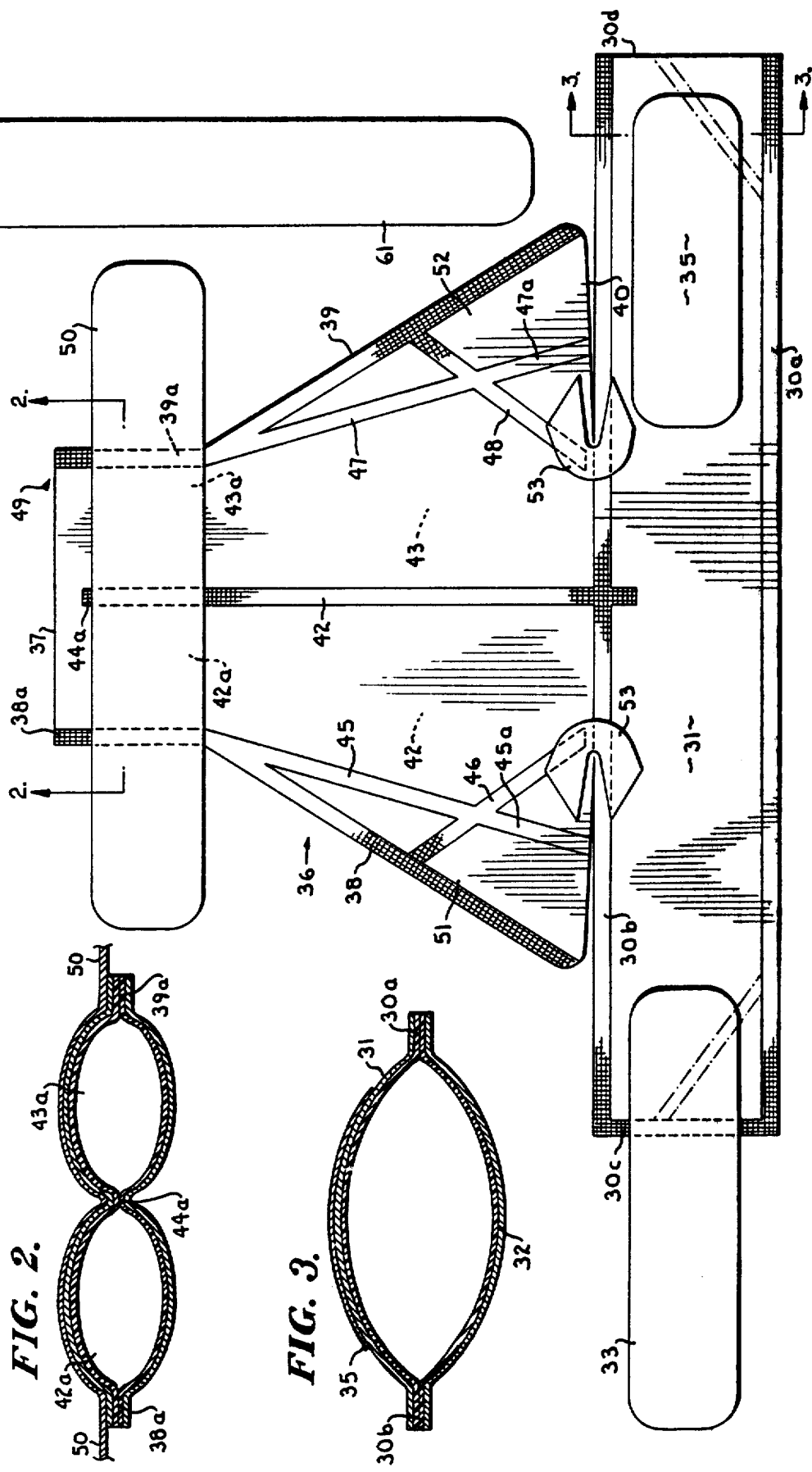
FIG. 2 is a view taken along the line 2—2 of FIG. 1 in the direction of the arrows with the walls of the blank expanded apart from one another for clarity in visualizing the separate sides thereof.
FIG. 3 is a view taken along the line 3—3 of FIG. 1 in the direction of the arrows with, again, the walls of the blank expanded away from one another to better illustrate the separate constructions thereof.

FIG. 4 is a vertical plan view of the blank of FIG. 1 taken from the opposite side thereof (the inside with respect to application to a patient), with the cells of the blank filled with heat exchanging materials and sealed to contain them. The protective layers on the attachment tabs are shown partly peeled back for illustrative and descriptive purposes. The view is cut away to better illustrate the contents (water bags and ammonium nitrate in the case of cooling heat exchange) in two places, specifically, the headband area (lower left hand of the view) and crown area (upper right center of the view). The extra attachment strap is shown to the left side of the view, included in the bracket, also inverted from the view in FIG. 1 and with its protective layers on the attachment tabs also partly peeled back.

FIG. 5 is a view taken along the line 5—5 of FIG. 4 in the direction of the arrows.

FIG. 6 is a view taken along the line 6—6 of FIG. 4 in the direction of the arrows.

Figure 7:
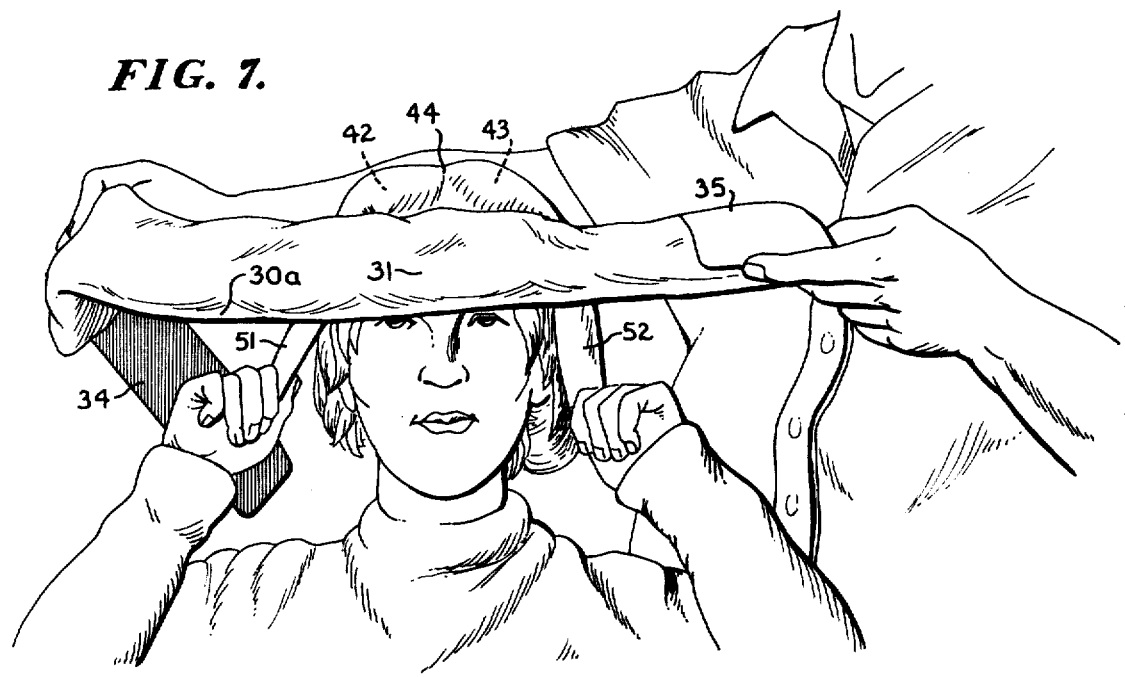

FIG. 7 is a front elevation of the device of FIGS. 4–6, inclusive, after activation of the cooling cells thereof, in first application to the head of the subject. Specifically, the crown portion of the device is laid on top of the subject's head with the subject grasping the tabs depending therefrom. The headband portion is shown grasped in the hands of an aide or helper for wrapping thereof around the subject's head.

Figure 8:
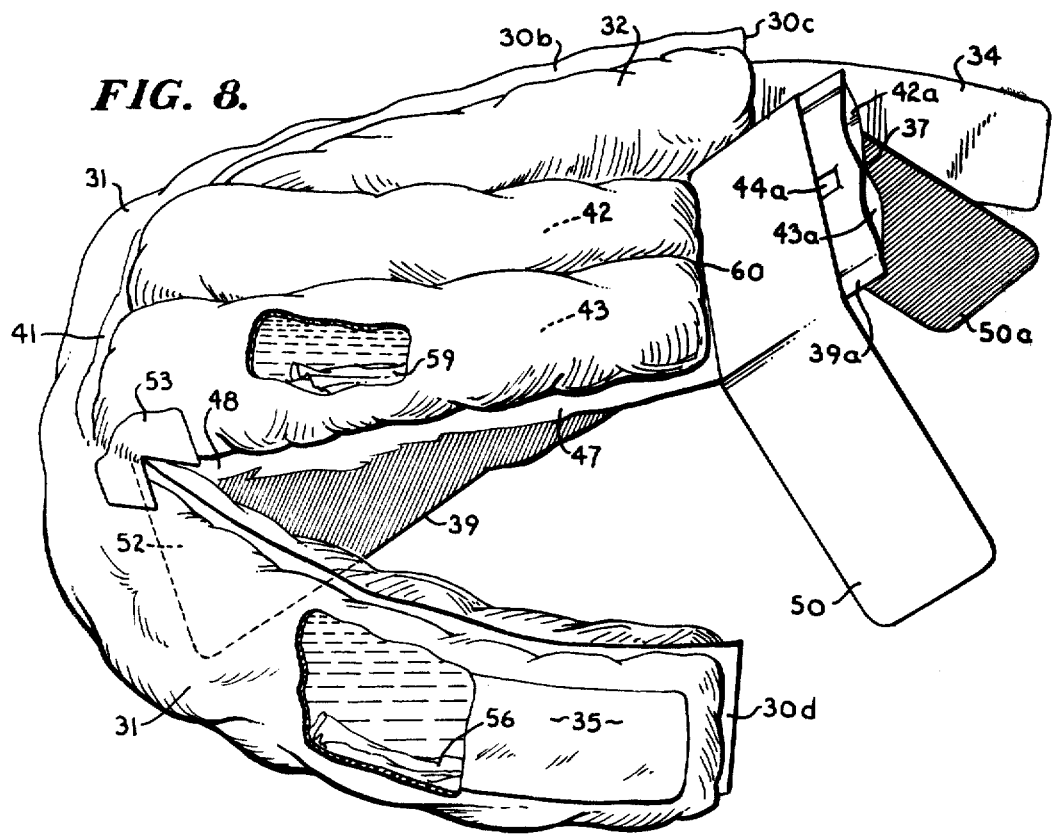

FIG. 8 is a three-quarter perspective view of the device of FIGS. 4–7, inclusive from above and slightly from the rear showing the activated device in a later stage of application (absent the head of the subject) as the headband is being wrapped about the subject's head. Portions of the crown and headband are cut away to illustrate the activated condition of the heat exchanging cells thereof.

Figure 9:
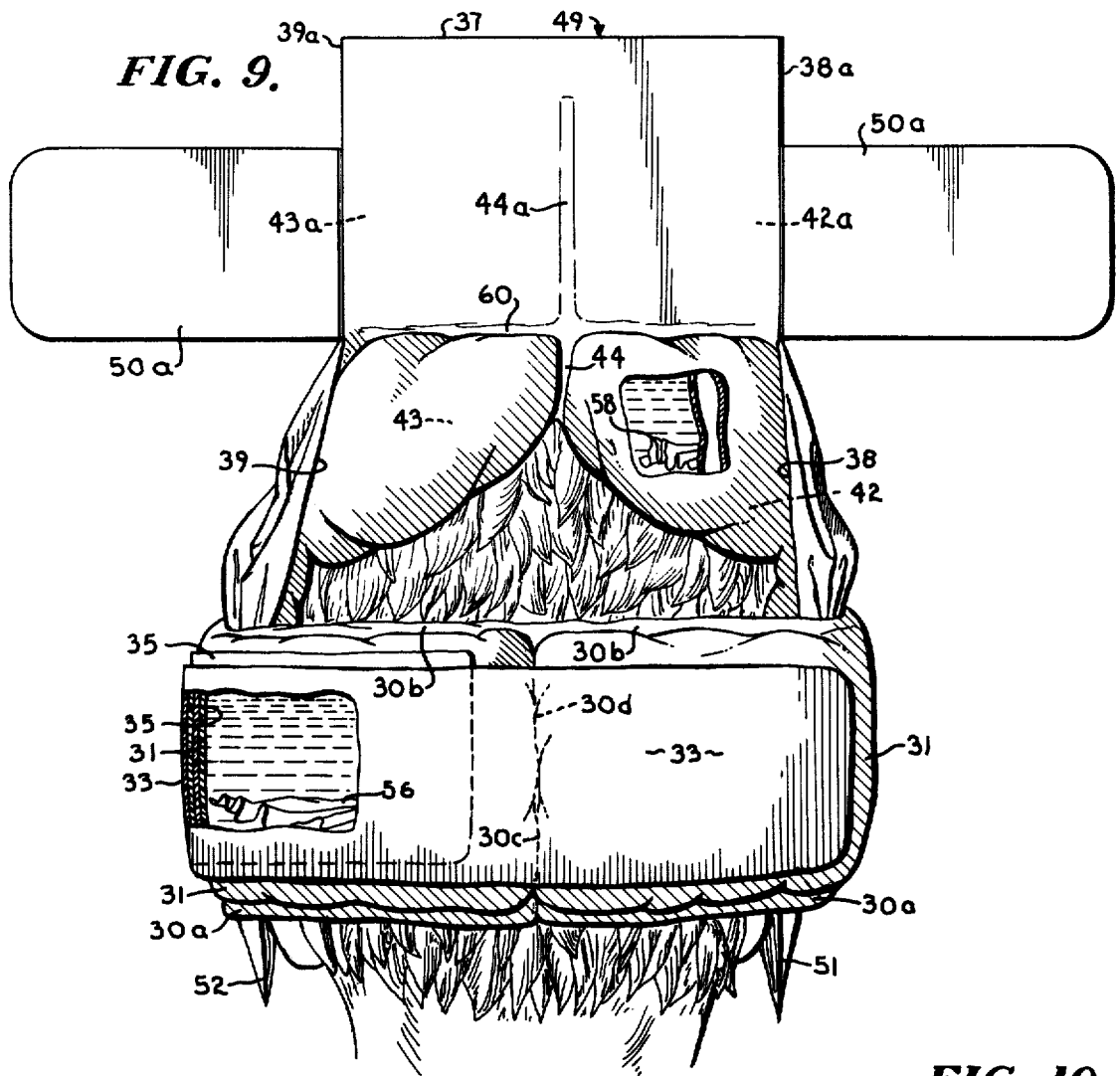

FIG. 9 is a rear view of the head of the subject of FIG. 7 after the headband has been applied and connected on the subject's head and before attachment of the crown portion rear top section flap to the rear portion of the headband. The structure of the headband and crown is cut away in two portions thereof, respectively, for illustrative purposes and the top section rear flap is raised upwardly from the subject's head for better illustration of the parts of the device at this stage of assembly.

Figure 10:
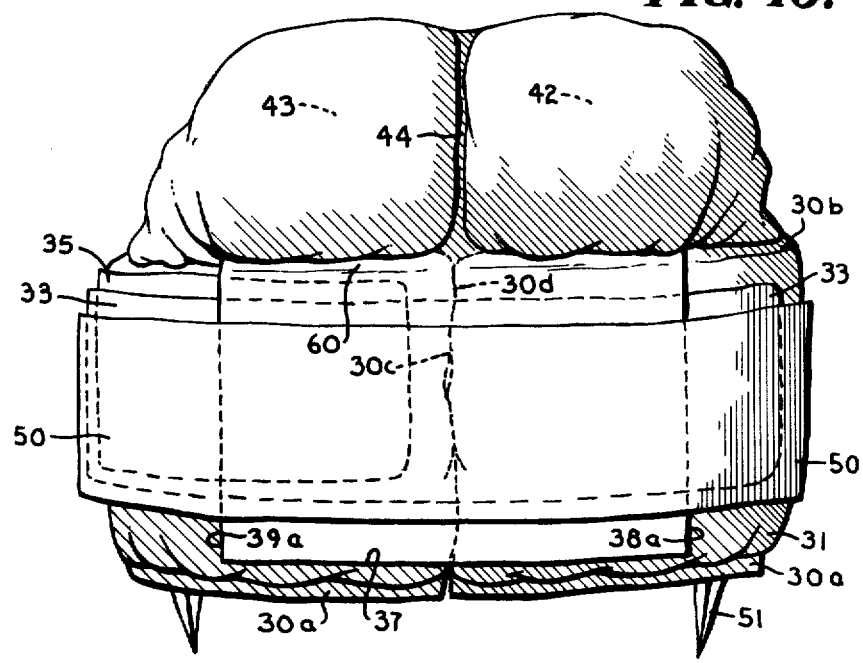

FIG. 10 is a rear view of the subject device in the stage following that of FIG. 9, with the top section rear flaps secured to the back of the headband. The device is complete, save for the addition of the final strap. While the head of the user is not shown, the device appears as it would were the user's head (as in FIG. 9) inside the device.

FIGS. 11-13, inclusive show the assembled device in three views, respectively front, rear and side views. In these views, the attaching straps have been somewhat lengthened and also spaced apart from one another for illustrative purposes to better show their relative positions and layering in the application of the device to the subject's head. In the views of FIGS. 9–13, inclusive, also, the thickness of the straps is exaggerated for illustrative purposes.

FIG. 11 is a front view of the device of FIGS. 4–10, inclusive in final or assembled form, being the stage immediately subsequent to that in FIG. 10 and following the stages of application of the final strap which are seen in FIGS. 14 and 15. A perspective view of the finally assembled device may be seen in FIG. 16. In FIG. 11, portions of the headband and crown are cut away to better illustrate the activated cell construction.

FIG. 12 is a rear view of the device of FIG. 11.

FIG. 13 is a side elevation of the assembled device of FIGS. 11, 12 and 16.

FIGS. 14–16, inclusive show, in the first two views, the final assembly or completion of application of the subject scalp heat exchanging device to a subject, this process resulting in the assembled construction seen in FIGS. 11–13, inclusive and 16. As just noted, the final figure of the three is the device in final application on the head of the subject in perspective, simplified view.

FIG. 14 is a three quarter perspective view from the rear from the subject of FIGS. 7 and 9 with the almost assembled construction of FIG. 10 placed on the subject's head, the subject shown grasping the top section (crown) side orientation tabs, as is the case during application, preferably, with the aide, whose arms are seen in FIG. 7, beginning application of the final strap onto the top of the subject's head and the crown portion of the device.

FIG. 15 is a three-quarter perspective view from the front of the subject of FIGS. 7, 9 and 14 with the aide making the final connection of the final strap on the opposite side of the headband from that seen in FIG. 14.

FIG. 16 is a three-quarter perspective view from the front and above of the subject with the cap finally completed on the subject's head and essentially adjusted for full scalp exchange.

(In the views of FIGS. 14–16, inclusive, details of the layering of the straps are not shown as they have been shown in previous views and the scale is much smaller.)

Figure 17:
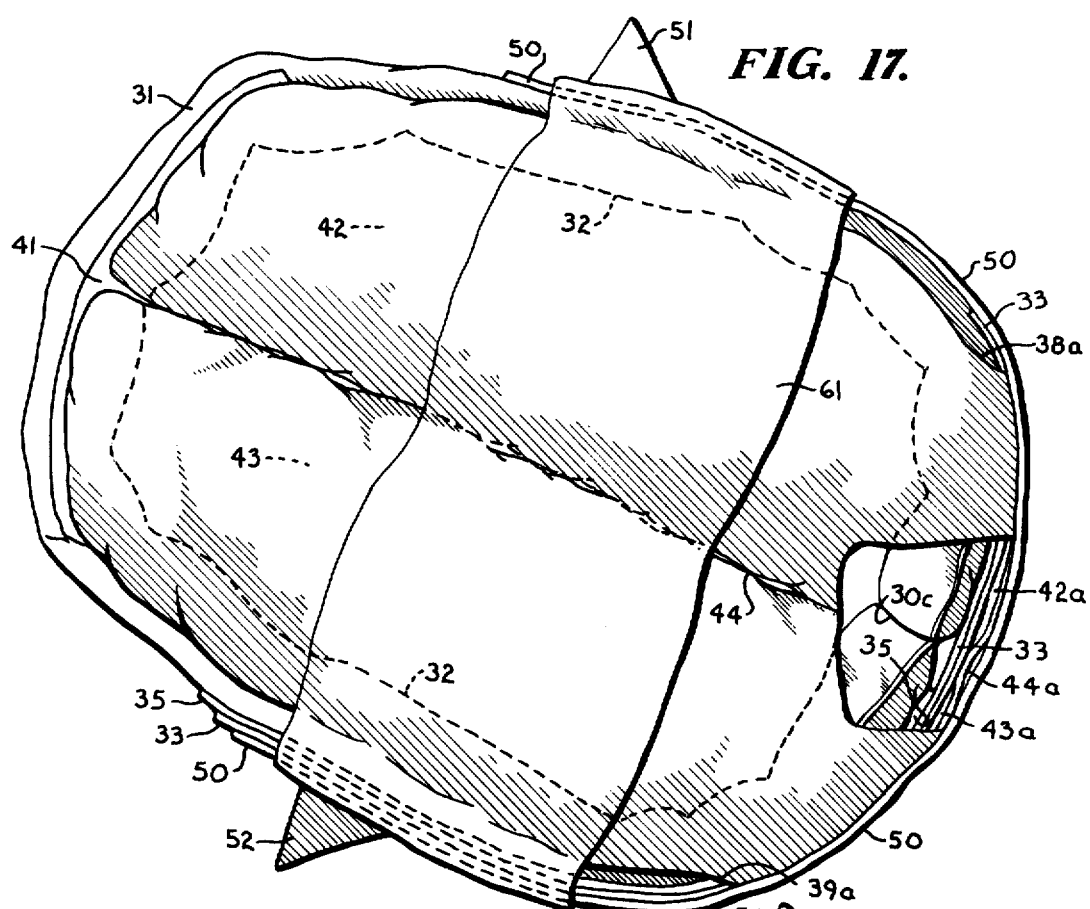

FIG. 17 is a top plan view of the assembled device of FIGS. 11–13 and 16 with a part of the crown portion thereof at the rear end cut away to better illustrate the structure and interconnection of the parts.

Figure 18:
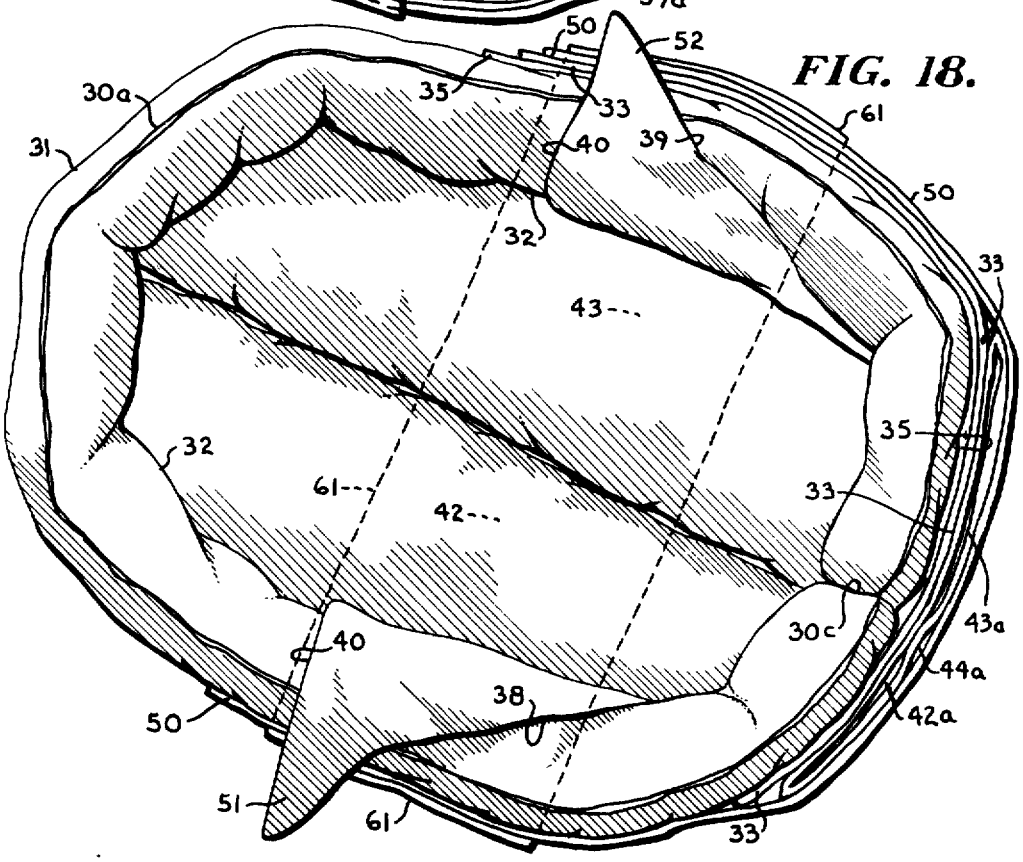

FIG. 18 is a bottom view of the assembled completed device of FIGS. 11–13, 16 and 17. (In the views of FIGS. 17 and 18, the front is to the left in the views and the rear to the right in the views.)

Figure 19:
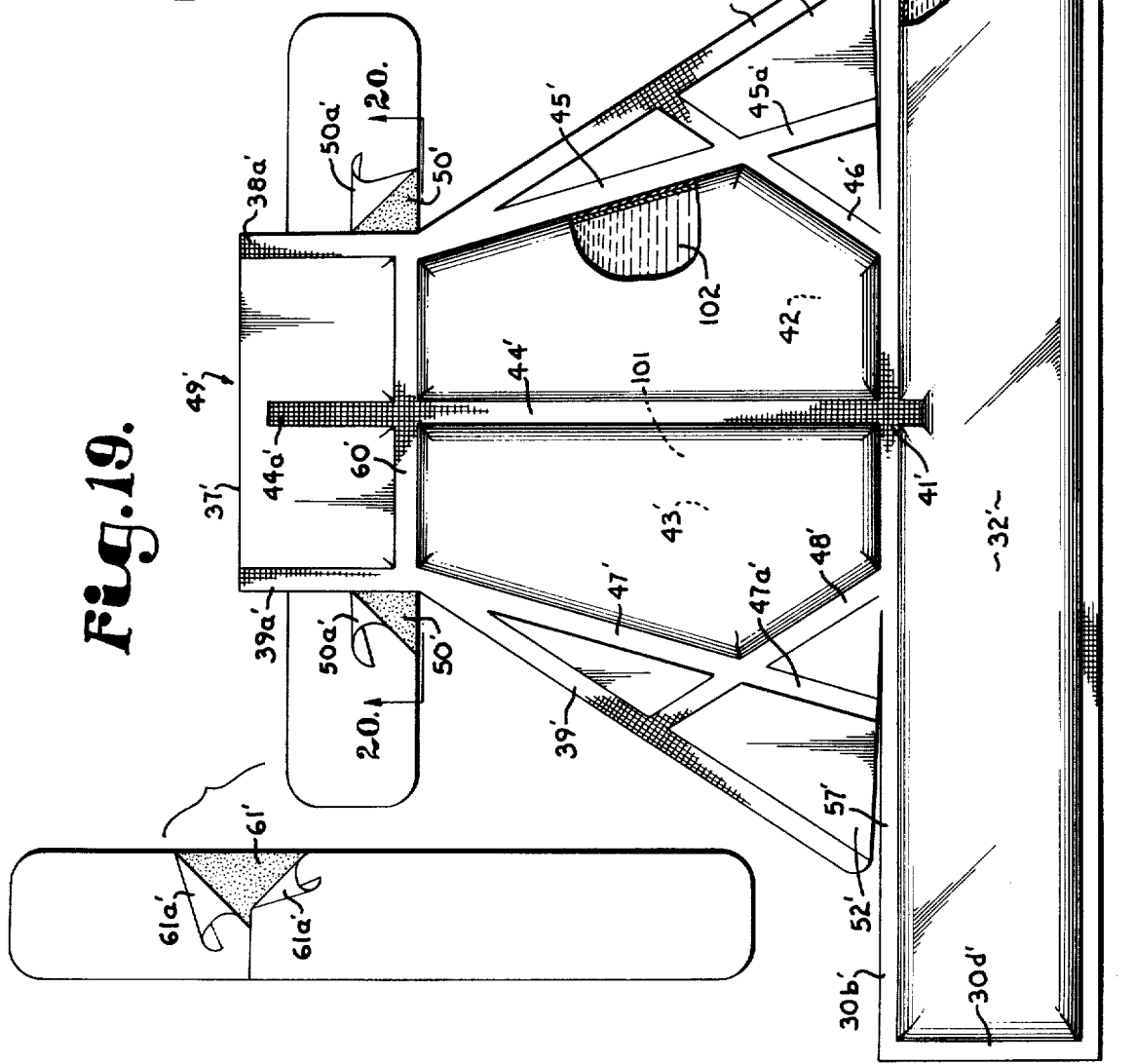

FIG. 19 is a view entirely equivalent to that of FIG. 4 with the exception that the heat exchanging means received in the sealed cells of the device comprise, instead of ammonium nitrate and a bag of water, a fluidic, repeatedly heatable or refrigerable chemical substance. [Thus, FIG. 19 is a vertical plan view of the blank of FIG. 1 taken from the opposite side thereof (the inside with respect to application to a patient), with the cells of the blank filled with the noted heat exchanging material and sealed to contain such. The protective layers on the attachment tabs are shown partly peeled back for illustrative and descriptive purposes. Portions of the figure are cut away to better illustrate the cell contents, specifically, the headband area (lower left hand of the view) and crown area (upper right center of the view). The extra attachment strap is shown to the left side of the view, included in the bracket defining FIG. 19, same also inverted in the view from FIG. 1 and with its protective layers on the attachment tabs also partly peeled back.]

Figure 20:
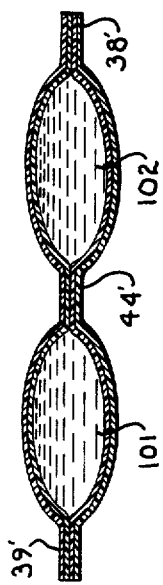

FIG. 20 is a line taken along the line 20—20 of FIG. 19 of the direction of the arrows.

Figure 21:
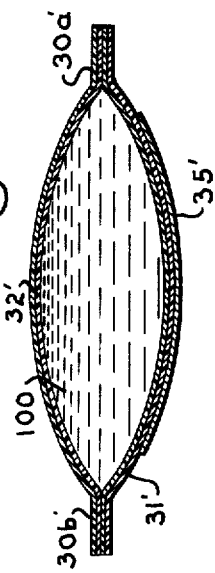

FIG. 21 is a view taken along the line 21—21 of FIG. 19 in the direction of the arrows.

RATIONALE OF THE INVENTION

In order to clearly and unquestionably understand the significance of the described and illustrated scalp heat exchanger, the following information is extracted and paraphrased from the Bean, Salmon and Griffith article mentioned in the above entitled section "The Prior Art".

The psychological impact of chemotherapy-induced alopecia (hair loss) represents one of the more devastating side effects of cancer chemotherapy. In some instances, the psychological consequences of this leads patients to refuse potentially curative chemotherapy. The hair loss problem is severe with the anthracycline antibiotic Adriamycin (Doxorubicin), a chemotherapy compound which has a spectrum of efficacy incompassing many types of cancer (e.g., breast, lung and ovary sarcomas, lymphomas and leukemias).

As early as 1973, an Abstract was published reporting good protection against Adriamycin-induced hair loss in 12 or 15 patients by regional application of chilled air to the scalp. More recently, the use of cryogel packs held on the scalp with stockingette produced good protection against hair loss over a short time in 20 to 40 patients on the same therapy.

It would appear that two advantages could accrue from cooling the scalp (scalp hypothermia). The first of these is vasoconstriction resulting from such, which decreases the amount of drug reaching the hair follicles. Secondly, Adriamycin (as numerous other drugs) requires temperature-dependent metabolic processes for cellular uptake and thus would have decreased action at reduced temperature.

The Bean et al study involved the prophylactic treatment of cancer patients receiving adriamycin-cyclophosphamide combination chemotherapy with a brief scalp hypothermia procedure at the time of each injection. The particle procedure described used crushed ice and disposable plastic bags. This treatment proved to be simple, inexpensive, well tolerated and universally available. It further proved to be quite effective at preventing hair loss and the patients studied had good or excellent preservation of scalp hair, usually obviating the need of wigs for cosmetic purposes. An even higher portion of patients receiving chemotherapy doses of lesser strength had good protection. Thus, it would seem that the protective scalp cooling was, to a certain extent, inversely related to dosage, so that a longer duration or more profound cooling might prove useful to consistently prevent hair loss at greater dosages.

In the actual Bean et al procedure, foam pads cut from the heels of disposable hospital slippers were placed over the patients' ears to insulate them against excessive cold exposure. Ice packs consisting of crushed ice in 60 by 60 centimeter plastic bags were applied (one in front, one in back) to cover the entire scalp. The ice packs were secured with 15 centimeter wide ace bandages wrapped in turban style. Such a turban was applied 5 minutes prior to each injection and left in place 30 minutes following the injection for a total of 35 to 40 minutes of scalp cooling.

The noted scalp iceing procedure reduced Adriamycin-induced hair loss substantially in relation to extensive prior historical experience with that drug combination. Good protection against hair loss was frequently maintained for the full 6 to 8 months period of drug administration. In the article, it should be noted, it was also hypothesized that a longer initial cooling interval perhaps should be employed.

PRIOR ART HOT AND COLD PACKS

The basic purpose of the subject invention is to cool the scalp areas of chemotherapy patients (together with limited scalp zone constriction) in order to prevent hair loss in cancer chemotherapy. However, the subject construction and development is not limited to such use or mere cooling. Specifically, that is, the entire construction may alternatively be used as a scalp heating cap, device or cover merely by substituting exthormic materials for the endothermic materials of a cooling application. In such use, the construction of application would be the same, however with heating produced rather than cooling.

Refrigerating and heating packages (cold packs and hot packs) of the type containing, within the outer pack, a dry chemical and a bag of water mixable therewith (on bursting of the water bag) to produce an endothermic or exothermic reaction, respectively, are well known to the art. The patent to Robbins, et al., U.S. Pat. No. 2,925,719, issued Feb. 23, 1960 for "Refrigerating Package" and the patent to Cailloutte, U.S. Pat. No. 3,643,665, issued Feb. 22, 1972 for "Therapeutic Pack For Thermal Applications" typically show the state of the art with respect to such. The water may be isolated from a chemical before activation by means other than bagging.

As noted, the prior art teaches chemical therapeutic packs which provide either reduced or increased temperatures by endothermic or exothermic chemical action, respectively. Conventionally, the components for such a reaction are both received within a plastic bag, separated from one another by an imperforate membrane. This membrane may be the outer bag itself crimped to divide the contents thereof or, alternative and typically, the liquid component of the reaction (typically water) may be provided in a second imperforate bag received within the first bag. In the latter case, the bag containing the liquid may, in operation, be pressurized sufficiently to burst itself by manually squeezing the inner bag through the unpressurized outer bag. This is the teaching of the Robbins et al. U.S. Pat. No. 2,925,719, supra.

As noted above, packs in accordance with the present invention may be employed to apply either cold or heat to the work object (the human head or a portion thereof) in the heat exchange, depending upon whether they contain chemical components for an endothermic or exothermic reaction, respectively.

It is well known in the art to provide (1) plastic films and laminate films (2) plastic film pouches, packages and containers and (3) heating or refrigerating package constructions of plastic film material. Typical materials making up such films include polyethylene, cellophane, polypropylene, polyester, etc. It is also known in the art to provide certain types of rupturable film packages and refrigerating packages, the latter seen in the Robbins et al. patent, supra. Since polyethylene and polypropylene are heat sealable, they are also commonly used as the internal member of a film laminate in a package construction, with a polyester or cellophane layer comprising the external laminate layer. Laminate films seemingly seal better, and the seals last longer, than simple, non-laminate film.

The Robbins et al. patent, supra, discloses a refrigerating package including an outer envelope formed of a suitable, flexible, fluid tight, sheet plastic material (for example polyethylene, vinyl or acetate), an inner envelope formed of the same material, a quantity of dry refrigerating chemical such as ammonium nitrate within the outer envelope and a quantity of water or other hydrous chemical disposed within the inner envelope. When the package is to be activated, an inward squeezing force is manually applied thereto so as to effect the rupture of the inner bag. Upon such rupturing of the inner bag, the water originally contained therein mixes with the dry chemical so as to result in a solution having a much lower temperature than the original temperature of the package.

The patent to Perino, U.S. Pat. No. 3,250,384, issued May 1, 1966, discloses (FIGS. 7–9, inclusive) cooling packages of the type described and, as well, various materials useful in the films for the respective containers thereof. It should also be understood that double wall polyethylene bags or multiple layer polyethylene bags or containers may be employed, particularly for the outer bag, in said cold and heat packs, as seen in the patents to Scholle, U.S. Pat. No. 2,898,027, Sachs U.S. Pat. No. 3,122,197, and, as well, the method patents to Anderson et al. U.S. Pat. No. 3,130,647 and Makraur U.S. Pat. No. 2,721,691.

The point to be made here is that the subject improved device may employ the heating and cooling packages of the type described whether (1) the chemicals in the bag are kept from one another by separate packaging or merely subdivision of the original package; (2) the outer container is single ply, multi-ply, a laminate of different materials, a plurality of plies of the same material or the like or (3) the inner container (if there is one) is single layered, multi-layered, multi-ply, laminate, weakened or the like.

Polyethylene, polyvinyl and polymylar films of one or more layers or laminates may conveniently be employed in this inventory. A layer of non-allergenic paper may conveniently be laminated thereto for comfort, better skin sensation and condensation absorption (as an outside layer).

DESCRIPTION OF THE BLANK

Referring first to FIGS. 1–3, inclusive, therein is shown the blank for the subject human scalp heat exchanger before the cells of the blank are filled with heat exchange materials for activation (preferably, water bags and ammonium nitrate, in the case of a cooling scalp heat exchanger). As previously described, FIG. 1 is a top plan view of this empty blank, while FIGS. 2 and 3 are views taken along designated lines of the blank with the walls of the blank expanded apart from one another for clarity in showing the separate sides thereof. In the views of FIGS. 2 and 3 and, as well, those of FIGS. 5 and 6, it can be seen that the walls of the blank and heat exchanger are laminates. That is, typically polyethylene or polypropylene on the inside with polyester or cellophane comprising the external laminate layer. For convenience in description, it will be assumed that each side wall of the portions of the blank or heat exchanger is a monolithic construction.

Referring, then, first to FIG. 1, at the bottom of the view is seen an elongate rectangular headband portion generally designated 30. (It should be understood that the views of FIGS. 1 and 4 are inverted from one another with FIG. 1, the empty blank, showing the outer surface of the blank before filling. This is the surface which is away from the patient's head which is to be heat exchanged. On the other hand, FIG. 4 shows the inside surface of the filled heat exchanger with heat exchanging materials, as will be described, in the cells thereof.

Headband portion 30, then, has lower edge 30a, upper edge 30b, sealed first end edge 30c and open and unsealed end edge 30d. Thus it is seen that there is a three sided seal (conventionally an ultrasonic weld or heat seal) for the elongate head band portion comprising, as mentioned, a double wall bag, each wall preferably a laminate of two films. For descriptive purposes, the outer surface of the outside wall of headband portion 30 is numbered 31 and the inside wall numbered 32. For attachment purposes, there is provided a first elongate tab 33 having on its free outboard portion (FIG. 4) an adhesive covering, removable sheet 34. At the other end on the outside surface of headband bag 30 is a tab 35 adhesively or otherwise attached to the outer surface 31 adapted to receive thereon the free end portion of tab 33 after removal of its adhesive cover for engaging purposes (and end abutment) with the end of the headband portion 30.

A crown portion generally designated 36 has a rearward (in use) end 37 (or end edge), side edges 38 and 39 and a forward or front edge 40 which is integral with or secured to the center of the upper edge of headband bag 30 with its own center portion which is generally designated 41.

In fabrication of this blank, two laminated sheets configured precisely the configuration of the overall sheet of FIG. 1 may be laid in alignment with one another and heat sealed at the sides, ends and edges, as well as interiorly thereof, to one another to give the blank configuration being described. This is the preferred and optimum method of fabrication. The seals may be heat seals, ultrasonic welds or other connections optimum to the plastic laminate sheets employed.

The crown portion 36 has three main parts. The first of these comprises the two center, forward cells 42 and 43 which are separated from one another and interiorly defined by seal 44. They are exteriorly defined by seals 45 and 46 on the left side of FIG. 1 and 47 and 48 on the right hand side of FIG. 1. It is important to note that seals 46 and 48 run into and are continuous with the upper edge seal 30b of headband portion 30 so that there is a complete front end seal of compartments or cells 42 and 43.

The second part of crown portion 36 is the rearward attachment flap, generally designated 49, and having parallel side edges 38a and 39a running the length thereof as a continuation of edges and seals 38 and 39 and two feed or loading channels 42a and 43a which are defined between the side edge seals 38a and 39a and an extension 44a of seal 44 into flap 49. A seal tab 50 having removable adhesive cover sheets 50a (FIG. 4) on the inside thereof is adhesively or otherwise fixedly attached to the outside surface of rear attachment flap 49 of crown portion 36.

The third part of the crown portion of the blank comprises the side grasping flaps 51 and 52 which are used by a patient in application as seen in FIGS. 7 and 15. These flaps are completely isolated from cells 42 and 43 by seals 45–48, inclusive. Additionally, for convenience purposes in manufacture, seals 45 and 47 are continued as at 45a and 47a to the front edge 40 of crown portion 46.

Thus it may be seen that what has been provided in the blank of FIGS. 1-3, inclusive comprises a multicelled, sealable blank defined by sealing together identical sheets of laminated plastic configured in a certain manner, each of the cells of compartments having an open end or edge for filling. Yet additionally, for structural integrity and rigidity at a possible point of tear (inboard end edges of edge 40 of the crown portion), reenforcements 53 of C configuration are adhesively or otherwise connected to the forward end of the crown portion and the upper outer face of the headband portion.

An optional diagonal seal, or two of them may be provided across the sealed end corners to reduce the internal capacity of the headband portion and better confine the materials in the headband in the working skin contacting portion to be described.

THE FILLED BLANK

With construction provided as shown and described in FIGS. 1-3, filling of the blank may take place. With respect to the headband portion 30, this typically involves, first, the insertion of one elongate water bag 54 into the open end edge 30 of the headband portion, the bag being pushed to the opposite end 30c. Thereafter, a quantity of heat exchanging chemical such as ammonium nitrate (55 in FIG. 4) is charged into the headband cell. Finally, a second water bag 56 is charged against the body of material and a heat seal 57 (FIG. 4) or other conventional type seal employed to weld shut the entire cell of the headband portion 30. Clearly, use of one or more bags in the cell is optional. Alternatively, for example, a charge of ammonium nitrate may be first inserted, then an elongate large size water bag, followed by a second charge of ammonium nitrate. The arrangement shown is that preferred from experience.

The charge of the cells 42 and 43 then takes place through passages 42a and 43a into end 37 of the crown portion. Elongate water bags 58 and 59 (FIG. 4) are passed into cells 42 and 43, respectively, and, as well, a charge of ammonium nitrate or other heat exchanging chemical. At this point, with each cell filled, a final heat seal 60 (FIG. 4) is made across seal 44 at the end of the convergence of side edges and seals 38a and 39a. Seal 60, addition to merging with seal 44 (which merges with seal or top edge 30b) also merges with seals 38a and 39a at its outer ends.

It additionally should be mentioned that, when the headband portion 30 cell is filled, as well as each of the cells 42 and 43 of the crown portion, before the final heat seal is applied, air is expelled, as far as possible, from the cells before the sealing thereof. This is to enable readily feasible bursting (by compression) of the water bags 54, 56, 58 and 50 and, additionally, permit fitting and shaping of the cells in application of the device to the patient's head as will be described below.

It should be noted that, as an alternative to the water-ammonium nitrate (for cooling) arrangement shown and described, the cells may be filled with repeatedly refrigerable gel-like compound of conventional type. This enables reusing of the subject scalp heat exchanger (insofar as such is desirable). However, while the device, with repeatedly refrigerable compound in the cells, will work, certain hazards have been noted such as possible frostbite and excessive chilling if the temperature of chilling of the device is not precisely controlled.

Again, one or more diagonal seals may be employed or provided at the sealed ends of the headband portion to somewhat reduce the interior capacity of the headband portion in its overlap zone and better confine the materials in the inboard head contacting zone. Such are seen in dotted lines in the blank illustration of FIG. 1.

DIMENSIONS

The following typical and optimum dimensions are given with respect to the previously described blank and filled scalp heat exchanging device. While the dimensions given are not absolutely critical, they are, indeed, optimum, functional for the purpose described and commercial. Additionally, quantities and capacities of ammonium nitrate and water for the respective cells are further hereinafter given in order that there be a full operative disclosure of one preferred form.

In order to give some concept of scale, the length of headband 30 may be substantially 29½ inches in blank, with its width 5½ inches. The length of the crown section in blank, from seal 41 to rear edge 37, may be 14½ inches. The width of crown rear end tab 49 may be 7 inches. The width of crown portion 36 at front edge 40 may be 19 inches. Tab 35 may be 9 inches in length, with the free flap portion engageable therewith of flap 33 8 inches. The free flap portions of adhesive flap 50 may be 5 inches on each side of crown end portion 49.

Typical quantities of water and ammonium nitrate in the headband portion 30 would be 650 grams of water in two 325 gram bag packages before a rupture and 650 grams of ammonium nitrate. In each of the crown section cells, a 225 gram water bag may be matched with 225 grams of ammonium nitrate. An alternate structure with closes limitation of the cell volumes employs (1) in the headband portion 600 grams of NH4 NO3, two 300 gram water bubbles and 60 grams binasal (thickener); (2) in the cap cells, each employs 200 grams NH4 NO3 and 20 grams binasal. Binesal 81 is a coarse granulation, pregdatinized tapioca starch vended by A. E. Staley Mfg. Co. of Decatur, Ill. 62525.

ACTIVATION AND APPLICATION OF SCALP HEAT EXCHANGER

To apply the device to a patient, assuming the heat exchanging medium is as illustrated (rupturable bags of liquid and dry mixing, exothermic or endothermic reacting chemical) the device first is activated. Alternatively, if rerefrigerable fluid fills the cells, it must be refrigerated or heated to the proper temperature (depending upon whether the heat exchange is heating or cooling). For purposes of description (and, of course, the primary object of the subject device, specifically, use with chemotherapy patients), a cooling function will be assumed.

The device may be laid down flat on the flat upper surface of a table in a manner of the illustration of FIG. 4 (or with the device inverted from the underside of orientation shown). The operator then, one by one, presses down on the water bags with the heel of one hand to activate (burst) them. The views of FIGS. 7-10, inclusive and 14-16, inclusive show most of the basic steps in assembly and application of the activated device to the head of a chemotherapy patient. Reference is here again made to the specific description of the drawing figures made herebefore.

After activation of each of the cells, the top or crown portion or section of the device is lifted up and placed on the top of the subject's head, with the wider front part 41 of the top section at the top of the patient's forehead, in order that the closed center section of the headband portion will naturally fall down over or in front of the patient's forehead. Referring to FIG. 7, as the crown portion is received on her (illustrated) head, the subject grasps the tabs 51 and 52 at the forward portion of the crown section just ahead of or opposite the subject's ears, at the direction of the aide or helper, whose hands may be seen in the view grasping the end portions 30c, 30d of the headband. The patient pulls downwardly on tabs 51 and 52, seating the crown section, at least in the forward and central portions thereof, on the forward and central portions of her head.

The aide or helper then, grasping the two free ends of the headband portion, pulls the sides thereof back along the side or temples of the subject's head over the tabs, which the patient continues to grasp and pull downwardly on. FIG. 8 shows a three quarter perspective view from the side and above of the left side of the device in the view of FIG. 7, illustrating the relative position of the parts as the aide pulls back the side sections of the headband to enclose the sides and temples of the subject's head. For simplicity, the head of the subject is not seen in FIG. 8.

Reaching the back of the subject's head with the headband and wrapping it around the patient's head immediately below the crown portion, the aide overlaps ends 30c and 30d (specifically, 30c over 30d). Protective tab 33a is then (or before) stripped from the headband flap 33 and, closely adjusting the top edge of the headband against the side edges of the crown portion and exerting a mild or considerable (depending on what is decided for the specific patient) constrictive effort on the headband, the aide rather tightly secures the headband portion around the head of the subject. It is important to note that, due to the depth of the headband, it overlies substantially the entire forehead of the patient and the temple and lower side portions of the head below the crown, ending at the rear on the lower curve of the cranial vault. Since the headband portion is filled with liquid, which precisely adjusts at every point to the shape of the subject's head in the headband portion, under the constriction, a complete encirclement with continuous contact and mild or stronger constriction is relatively easily made.

At all times, the subject maintains a grasp on the crown portion tabs 51 and 52, tugging them downwardly, so as to maintain firm crown section contact and a firm location of the entire crown section so that the aide or helper can locate the headband portion properly with respect to not only to the head of the patient, but also the activated bags in the crown section. FIG. 8 shows the back end and rear tab portion 49 of crown section 36 angled upwardly, with attaching tab 50 raised above the headband portion which is being drawn back around the subject's head. FIG. 9, on the other hand, shows the headband encirclement completely made and the flap 33 firmly adhesively engaged over tab surface 35. In FIG. 9, the rear end of the crown portion activated bags 42 and 43, the entire flap 49 and flap members 50 are shown lifted up for viewing purposes. It is especially noted, additionally, that tabs 51 and 52 are extending downwardly under the headband side portions. The hands of the patient are not showing grasping the tabs, but would be at this point.

Moving from the showing of FIG. 9 to that of FIG. 10, the headband portion encirclement and engagement having been fully made, the helper first removes adhesive covering members 50a from the engaging flaps on end piece 49 and pulls down the rear flap or tab 49 of crown portion 36 over the rear outer surface of the secured headband. It is most important at this juncture that the operator or aide adjust the height of the headband and its position around the head of the subject at the desired level front, sides and back. This includes essentially an entire forehead overlap, an ear overlap and the bottom part of the skull overlap at the rear. (At this juncture, it may be mentioned that, typically, insulating sleeves may be slipped over the subject's ears to protect them from excessive chill, if needed or desired.) During this adjustment, at all times, the subject properly grasps the ear tabs to keep them pulled down and the top section pulled against her head.

After this leveling is achieved, the aide, having stripped the protective covers from the crown section rear flap side attachments, pulls the top section rear flap 49 firmly down over the rearmost outer surface of the headband portion and attaches this flap by its tabs to the headband. While this is done, the subject is holding onto the crown section side or ear tabs. FIG. 10 shows the near completed heat exchanging device with the headband portion first tension (constriction) secured and the crown section thereafter secured thereto and thereover. The assemblage will not now fall off the subject's head, but it is incomplete because (1) the side edges or walls of the top section heat exchange bags have not been brought into complete abutment with the side top walls or edges of the headband cell in continuous contact and (2) the top cells of the crown section have not centrally been brought together in wall-to-wall contact to remove any possibility of a center head holiday or non-cooled area.

The accomplishment of the last two purposes is achieved by application of one or more free adhesive straps 61 from one side face of the headband, over the crown section to the other side face of the headband at about the ear level. This process is seen in FIGS. 14–16, inclusive. In FIG. 14, the aide, helped by the patient pulling down on the ear tabs, snugs the headband upwardly and the adjacent crown cell downwardly so that their side top and lower walls or edges firmly abut continuously one against the other. That is, a first adhesive attachment is made between the adjacent side portions of the headband cell and the crown cell next thereto.

The next attachment is at the center seam of the two crown cells which are drawn together, one against the other with the adhesive flap laid over the both of them, securing them in wall-to-wall abutment. Finally, FIG. 15, the other outer wall of edge of the other crown section cell is firmly abutted against the top wall of the headband portion cell and adhesively secured thereagainst. During this entire operation, the subject continues to hold the ear tabs. Thus, the helper successively aligns and contacts the adjacent edge walls of the adjacent cells, one with the other, and adhesively secures them in such contact from headband to top cell, top cell to top cell and top cell to headband cell over the top of the head.

FIG. 16 shows a view from the front of the subject with the completed heat exchanging device on her head. The cap device now comprises a unit held together by (1) the headband to headband tab, (2) the crown section rear flap to headband tab and (3) the center over the top adhesive band which is headband to crown cell, crown cell to crown cell and crown cell to headband. With this assemblage, the unitary device may be adjusted to final precision and comfort for the user-wearer with full hair area contact, as well as full forehead contact, as clearly seen in FIG. 16. With the assembly operation carried out, as described, not only is there provided constriction around the entire headband (as well as cooling from the headband into the constrictive zone), but also compaction on the entire top of the head from the completed cap with the cells of the headband and crown section compressed, one against the other and held down against the patient's head. Thus entire head heat exchange, as well as overall head compaction or compression and headband constriction, are all achieved in adjustable fashion for each individual user and patient.

INTEGRATED DEVICE DESCRIPTION

The subject heat exchanging head piece for cooling or heating the entire scalp (hair bearing) area of the human head comprises, in combination:

(1) An elongate, substantially rectangular headband portion 30 which is adapted to continuously and circumferentially wrap around a human head, including the forehead, the temple-ear head side zones and the lower back portion of the cranial vault. The headband portion has substantially parallel, spaced apart, opposed upper and lower edges 30a and 30b and end edges 30c and 30d, the latter substantially at right angles to the former.

(2) Means 33 and 35 are provided, engageable between the free ends of the headband portion 30, which are adapted to secure the said headband free end portions 30c and 30d together, one against the other, to form a continuous, optionally (but preferably) compressive or constrictive headband.

(3) The headband portion comprises an elongate, hollow bag of sealed, liguid tight construction, the bag filled with materials (54, 55, 56) for heat exchange.

(4) A crown portion for said head piece is provided, having a forward edge 40 secured centrally (41) to the substantial center of the top edge 30b of the headband portion, side edges 38 and 39 extending rearwardly from the said forward edge securement and end edge 37 spaced rearwardly from and substantially parallel to forward edge 40, 41. Crown portion 36 comprises at least one elongate, hollow bag (here two bags 42 and 43) of sealed, liquidtight construction. Each bag is filled with material (58, 59 and 58a, 59a) for heat exchange.

(5) Means are provided at the rear edge 37 of crown portion 36 (as at 50) which are adapted to secure the crown portion rear end to a part of the headband portion substantially 180° away from and opposed to the crown portion forward edge securement to the headband portion (at 41).

(6) Means 61 are provided for securing the side upper edges of headband portion 30 to the side edges of the crown portion bags 42, 43, whereby to form (when the end edges of the headband portion 30 are secured together, the rear edge 37 of the crown portion 36 is secured to the headband and the side upper edges 30b of headband portion 30 are secured to the side edges 45 and 46, 47 and 48 of the bags 42 and 43 of the crown) a continuous, scalp contacting head piece for completely and uniformly heat exchanging the hair bearing area or zone of the human scalp.

The entire headband portion 30 preferably comprises a single, continuous, elongate, rectangular hollow bag sealed continuously and circumferentially thereof at the side and end edges thereof. Headband portion 30 is most preferably longer than the circumference of the patient's head it is to encircle, so that the end edges 30c and 30d thereof abut and somewhat overlie one another when the headband portion is secured around the patient's head in use. In a one-shot application of the subject device, the heat exchanging materials 54-56 in the headband portion preferably comprise two elongate, rectangular, water containing bags 56 and 54 adapted to be pressure ruptured, (the bags, before activation, positioned one adjacent each end edge 30c, 30d of the headband portion 30) and dry chemical 55 such as ammonium nitrate adapted to react with the water on rupture of the bags to provide an endothermic reaction. The means 33, 35 for securing the headband portion end edges 30c, 30d together preferably comprises an elongate flap having adhesive material on one side thereof for adhering to the outer walls of the headband portion free edges and areas of the headband next thereto and a tab 35 area secured to the outer surface of the headband adjacent one end to provide secure adhesive engagement with flap 33.

The crown section 36 of the subject heat exchanging head piece is preferably divided into two elongate, hollow bags 42, 43 of sealed, watertight construction, the bags containing materials (58, 58a, etc.) for heat exchange. Crown section 36 is preferably divided centrally into aligned, substantially equal size elongate bags 42, 43 of liquid tight construction running lengthwise substantially at right angles to the front edge connection 41 of the headband 30 and crown 36 portions. Substantially triangular tab portions 51 and 52 are preferably provided at each one of the side edges (45, 46 and 47, 48) of crown portion 36 adjacent the front edge connection 41 thereof.

The means 50 at the rear edge 37 of crown portion 36 adapted to secure the crown portion rear end to a part of the headband portion preferably comprises a rearwardly extending tab extension 49 of crown portion 36 adapted to overlie (outside of) and lie against the free end secured portion of the headband 30 (after the end edges 30c, 30d of the same have been secured to one another) and be attached thereto. Tab extension 49 can underlie, but most preferably overlies the secured headband end edge portion prior to engagement connection therewith. Adhesive flap 50, having adhesive material on the inboard side thereof, is adapted to secure the crown portion tab 49 on headband portions 30d and 30c (outside of the ends thereof after connection) together.

The means 61 for securing the side upper edges of the headband portion to the side edges of the crown portion, whereby to form a continuous, scalp connecting head piece, preferably comprises at least one elongate strap 61 adhesively or otherwise engaged between the side edges of the headband portion and the side and top faces of the crown portion on each side of the head piece. In such case, the top side edges of the headband portion must be abutted against and essentially joined to the bottom side edge portions of the crown portion. This connection and adjustment can be made with only one elongate strap communicating from the side headband portion on one side to the opposite side headband portion over the crown, the strap secured to all three noted portions (opposed headband portions and crown). Two elongate straps of the character described, spaced apart from one another on the headpiece, may also secure the side edges of the headband at the upper portion thereof to the side edges of the crown at the side extremities thereof to make an integral, uninterrupted head piece. The latter would be the case with an extremely long head structure or some other unusual size and/or head shape problem.

As an alternative to the one shot, liquid bag-ammonium nitrate or other dry chemical system, a fluidic, repeatedly refrigerable chemical substance may fill the single cell of the headband portion and the two cells of the crown portion.

FIGS. 19-21, INCLUSIVE

FIGS. 19-21 show three views of the subject device showing same adapted to use, as an alternative to the one shot, liquid bag-ammonium nitrate (or other dry chemical) system, a fluidic, repeatedly refrigerable or heatable chemical substance filling the single cell of the headband portion and the two cells of the crown portion. In the views, all of the parts identical between FIGS. 4-6, inclusive and the subject figures are numbered the same, but primed. The only additional numbers with respect to these figures are as follows:

(1) The number 100 is used to indicate the said fluidic, repeatedly refrigerable or heatable chemical substance filling the cell in the headband;

(2) The numerals 101 and 102 show the, or refer to the same substance in the two crown cells.

Since the structure (as noted) is substantially identical and the function is the same, as well as the application of the device to a patient, no further description of either will here be made or remarked. However, as noted in the general remarks hereafter, for a patient's safety, it is necessary to both carefully control the freezer temperature (or heater temperature) and, as well, test the heat exchanging device as to temperature before application.

GENERAL REMARKS

According to the best available records, some 75 million chemotherapy doses was given last year in the United States of America (1979). Additionally, this number has been increasing, from year to year. One of the earlier forms of the subject device employed a chin tie or under-the-chin tie to maintain the device cinched or tightly applied to the subject's head. However, because of the possibility of vomiting problems during chemotherapy, this use and employment is not feasible.

It is also not feasible, indeed not possible, to apply the subject heat exchanging device without a helper and without the patient or subject holding the top section ear flaps for stability and positioning during application. If the patient or subject is not sufficiently well or available or able to help by holding the top section ear flaps, then two operators or helpers are usually required to apply the cap to the subject.

The subject device preferably employs surfaces of non-allergenic sulfide paper laminating to polyethylene. The purpose of the use of such paper surfacing in hospital products is to minimize water condensation. Thus, condensation on the patient's head and, as well, the patient's hospital gown, any towels used or sheets when the patient is in bed, are minimized.

The most optimum time of application before and after the chemotherapy injection, as well as during the injection and, yet further, the best temperature of application remained to be decided. At the present, it is believed that 15 minutes before the injection, 30 minutes during the injection and 15 minutes thereafter are optimum or, at least, minimum. The 28° F. temperature of an efficiently used water-ammonium nitrate pack produces good results.

With respect to results, the results found in the Beam et al article are, at the least, to be expected. At the very worst (under the most rigorous conditions of chemotherapy to a given patient, depending upon the patient's condition and the intensity and frequency of dosing) the subject device minimizes hair loss.

By employing a refrigerable (rerefrigerable) compound, the subject device may be made reuseable. This approach, as noted, raises certain problems, including excessive chilling. To some extent, at least, hospitals do not prefer (necessarily, that is, depending upon the circumstances) reuseable devices. To some extent this may be because of convenience of billing procedures to the patient, but also, cleaning and cross-contamination problems, as well as storage, must be considered. Additionally, the provision of refrigeration devices reasonably adjacent to application points must be considered in this variation.

We have discovered that it is optimum to have the headband portion closed and continuous at the front, as well as a continuous cell for the headband. With respect to the former, one wants full, continuous heat exchange of the forehead zone because of the numerous blood vessels passing therethrough. With respect to the second, in the event or occasion of seams or breaks in continuity of the headband portion, because the headband portion is stretched to give constriction around the head, it would extremely difficult, or well nigh impossible to avoid holidays or nonheat exchange zones. Accordingly, the continuity around the head. Since the headband must be open for application and adjustability purposes in its length, the cell making up the headband must be of sufficient length that it overlaps at the rear of the patient's head for continuity of head exchange and cooling.

There should not be any hot spots or holidays in an applied cooling cap. This is first accomplished by having all the cells (headband and crown portions alike) so full that, in the applied cap, full coverage of the hair growing area of the head (scalp) can be obtained and, yet, continuous abutment of one cell to the other (headband to top cells and top cells to top cells) can be accomplished. It should be noted that the headband to top cell abutment must be made not only at the lateral or side portions of the head, but also at the forehead and rear. The top cell to top cell abutment is effected centrally of the top of the head. Hot spots or seams in the heat exchanging device will result in hair loss in the pattern of the seams.

The subject device has two or more head size adjustments. The first of these effected is the hat band or headband adjustment in the headband portion, per se. This is a complete circle of compression on all blood vessels leading into the scalp. The second adjustment is the crown size. These adjustments are effected sequentially, that is, the hat size is the first adjustment completely made and, thereafter, the crown size. If the cells of the device are not first activated (in the case of a one-shot type device), then the sequential adjustments could not be made, as well as the edge to edge adjustments at the seams.

Of course, it would be most difficult to break the water bags with the device placed on the patient's head, even by squeezing. In effect, breaking the water bags makes uniform the contents of each of the cells with respect to fitting on the head. The packed water bags would prevent this prior to activation. One must also consider a volume loss in the mixing and dissolving of ammonium nitrate in the water on activation.

Further arguments in favor of securing the headband portion at the rear of the head lie in the fact that the forehead is higher than the lower rear portion of the skull. Thus, the activated fluid in the headband cell, when the securement is at the rear of the head at the base of the skull, tends to fill the entire cell, particularly at the base end. In the case of reversal, with securement on the forehead, the fluid would tend to pool at the lower rear portion of the head and, additionally, there would be the hazard of the operator working in the vicinity of the patient's eyes.

The subject device is not useful in leukemia, because of the circulating cancer cells in the blood.

It is important to realize that, while it is desirable to have some pressure in all zones of the heat exchanging device, in contact on the head, and particularly in the headband for limited constriction of the vessels going into the head, one definitely wants to avoid the creation of a tourniquet effect which can result in pain, fainting, psychological effects and possible damage to some blood vessels.

For proper distribution of the activated liquid contents in the crown portion of the device, it is best that it be segmented into two cells. Such segmentation may be front to back or side to side and equally effective. However, the latter is harder to fill and, additionally, provide an integrated, easy to apply device. What is necessary in the crown portion is both confinement of fluids and distribution. Yet further, by manipulation of the pack as described in application, the cell abutment of one to another in the crown portion and with the headband cell is absolutely necessary for continuous cooling or heat exchange surface and body.

With respect to the reuseable, freezer type pack, as several times previously noted, the problem is that a temperature of $-10°$ F. could inadvertently be reached, with frostbite resulting. This means that it is necessary to both carefully control the freezer temperature (if such were to be used in the hospital or clinic) and, as well, test the heat exchanging device's temperature before application. At present, using the ammonium nitrate-water combination, a minimum temperature of 28° F. is provided, which does not give frostbite. A workable mixture (but not limiting) is 50-50 percent ammonium nitrate and water by weight. It should be noted that, with respect to the ammonium nitrate-water packs, the ambient temperature at which the devices are stored relate to the water heat when activated and thus the ultimate temperatures reachable.

Ear covers of any simple construction and any insulating material (ex) polyethylene foam may advantageously used to minimize excess chilling or heating of a patient's temperature sensitive ears. They are applied before application of the headband. None are shown in the views to minimize confusion between layers of material.

From the foregoing, it will be seen that this invention is one well adapted to attain all of the ends and objects hereinabove set forth together with other advantages which are obvious and which are inherent to the apparatus.

It will be understood that certain features and subcombinations are of utility and may be employed without reference to other features and subcombinations. This is contemplated by and is within the scope of the claims.

As many possible embodiments may be made of the invention without departing from the scope thereof, it is to be understood that all matter herein set forth or shown in the accompanying drawings is to be interpreted as illustrative and not in a limiting sense.

We claim:

1. A heat exchanging head piece for cooling or heating the entire scalp (hair bearing) area of the human head, comprising, in combination:
   an elongate, substantially rectangular headband portion adapted to be continuously and circumferentially wrapped around a human head, including the forehead, the temple-ear head side zones and the lower back portion of the cranial vault,
   said headband portion having substantially parallel, spaced apart, opposed upper and lower edges and end edges, the latter substantially at right angles to the former, as well as two free ends at the end edges thereof,
   means engageable between the free ends of the said headband portion adapted to secure said free ends together, in contact with one another, to form a continuous headband,
   said headband portion comprising an elongate hollow bag of sealed, liquidtight construction, said bag containing materials for heat exchange,
   a crown portion for said head piece having a forward edge secured centrally to the substantial center of the uper edge of the headband portion, side edges extending rearwardly from the said forward edge securement and an end edge spaced rearwardly from and substantially parallel to the forward edge,
   said crown portion comprising at least one elongate, hollow bag of sealed, watertight construction, said bag containing materials for heat exchange,
   means at the end edge of said crown portion adapted to secure said end edge to a part of the said headband portion substantially 180° away from and opposed to the crown portion forward edge securement to the headband portion, and
   means for securing the upper edge of the headband portion to the side edges of the crown portion whereby to form, when the end edges of the headband portion are secured together, the end edge of the crown portion is secured to the headband portion and the upper edge of the headband portion are secured to the side edges of the crown portion, a continuous scalp contacting head piece for completely and uniformly heat exchanging the hair bearing zone of the human scalp.

2. A head piece as in claim 1 wherein the entire headband portion comprises but a single, continuous, elongate, rectangular hollow bag sealed continuously and circumferentially thereof at the upper and lower and end edges.

3. A head piece as in claim 1 wherein the said headband portion is sufficiently long that the end edges of the headband portion will abut and somewhat overlie one another when continuously and circumferentially wrapped around a human head.

4. A head piece as in claim 1 wherein the entire headband portion comprises but a single, continuous, elongate, rectangular hollow bag sealed continuously and circumferentially thereof at the upper, lower and end edges,
   said headband portion being sufficiently long that the end edges thereof abut and somewhat overlie one another when continuously and circumferentially wrapped around a human head.

5. A head piece as in claim 1 wherein the means for securing the headband portion end edges together comprises an elongate resilient flap having adhesive material on one side thereof, said flap overlying and adhering to portions of the outer walls of the headband portion adjacent the free ends thereof.

6. A head piece as in claim 1 wherein the heat exchanging materials in the headband portion comprise at least one water containing bag which is itself adapted to be pressure ruptured and dry chemical material adapted to react with the water produced from the rupture of the bag in order to provide a heat exchanging reaction.

7. A head piece as in claim 1 wherein the heat exchanging materials in the headband portion comprise two water containing bags which are each adapted to be pressure ruptured, said bags positioned one adjacent each end edge of the headband and a quantity of dry chemical material adapted to react with the water on rupture of the bags containing said same to provide a heat exchanging reaction.

8. A head piece as in claim 1 wherein the heat exchanging materials in the headband portion comprise a fluidic chemical substance adapted to be refrigerated for cooling purposes or heated for heating purposes.

9. A head piece as in claim 1 wherein the heat exchanging materials in the crown portion comprise at least one water containing bag adapted to be pressure ruptured, and a quantity of dry chemical adapted to react with the water on rupture of the bag to provide the heat exchange reaction.

10. A head piece as in claim 1 wherein the heat exchanging materials in the crown portion comprise two water containing bags each adapted to be pressure ruptured, said bags positioned spaced apart from one another and a quantity of dry chemical material adapted to react with the water on rupture of the bags to provide a heat exchanging reaction.

11. A head piece as in claim 1 wherein the heat exchanging material in the crown portion comprises a fluidic chemical substance adapted to be refrigerated for cooling purposes or heated for heating purposes.

12. A head piece as in claim 1 wherein the heat exchanging materials in the headband portion bag and crown portion bag comprise a fluidic chemical substance which is refrigeratable for cooling purposes or heatable for heating purposes.

13. A head piece as in claim 1 wherein the crown portion is divided into two elongate, hollow bags of sealed, liquid tight construction, said bags each containing materials for heat exchange.

14. A head piece as in claim 13 wherein each said crown portion bag contains a sealed, water containing bag adapted to be pressure ruptured and a quantity of dry chemical adapted to react with the water on rupture of the bag to provide a heat exchanging reaction.

15. A head piece as in claim 13 wherein the heat exchanging materials in each said crown portion bag comprise a fluidic chemical substance adapted to be refrigerated for cooling purposes or heated for heating purposes.

16. A head piece as in claim 13 wherein the crown portion is divided centrally into two aligned, substantially equal sized, elongate bags of sealed, liquid tight construction running lengthwise substantially at right angles to the connection of the headband and crown portions.

17. A head piece as in claim 16 wherein the heat exchanging materials in each crown portion bag comprise a water containing bag adapted to be pressure ruptured and a quantity of dry chemical adapted to react with the water on rupture of the bag to provide a heat exchanging reaction.

18. A head piece as in claim 16 wherein the heat exchanging materials in each crown portion bag comprise a fluidic chemical substance adapted to be refrigerated for cooling purposes or heated for heating purposes.

19. A head piece as in claim 1 including a substantially triangular tab portion connected to each one of the side edges of the crown portion adjacent the connection thereof to the headband portion,
    said tab portions opposed to one another and of greater length than the width of the headband portion in order to extend downwardly below the latter for grasping by the user in application of the head piece.

20. A head piece as in claim 1 wherein the means at the end edge of the crown portion adapted to secure the crown portion end edge to a part of the headband portion comprises a rearward tab extension of the crown portion of sufficient length and width that it is able to lie against a substantial portion of at least one of the free ends of the headband portion after same has been secured to one another, so that said tab extension may be connected thereto.

21. A head piece as in claim 20 wherein the said crown portion tab extension overlies the outer surfaces of the said secured headband portion end edges and is fixedly attached thereto.

22. A head piece as in claim 21 wherein said tab extension includes a flap extending on each side thereof having adhesive material on one side thereof adapted to be secured to the outer surfaces of the headband portion, thereby securing the crown portion tab extension to said headband portion.

23. A head piece as in claim 1 wherein the last securing means recited therein comprises at least one elongate strap connecting the upper edges of the headband portion and the adjacent side edges of the crown portion on the opposite sides of the head piece together with one another.

24. A blank for a heat exchanging head piece for cooling or heating the entire scalp (hair bearing) area of the human head comprising, in combination:
    an elongate, substantially rectangular headband portion adapted to be continuously and circumferentially wrapped around a human head including the forehead, the temple-ear head side zones and the lower back portion of the cranial vault,
    said headband portion having substantially parallel, spaced apart, opposed, upper and lower edges and end edges, the latter substantially at right angles to the former, as well as two free ends at the end edges thereof,
    said headband portion comprising an elongate hollow bag of sealable, liquidtight construction having one end edge thereof open for filling purposes,
    a crown portion of said head piece having a forward edge secured centrally to the substantial center of the upper edge of the headband portion, side edges extending rearwardly from the said forward edge securement and an end edge spaced rearwardly from and substantially parallel to the forward edge,
    said crown portion comprising at least one elongate hollow bag of sealable, watertight construction,
    at least a portion of the end edge of said crown portion opening into said sealable, watertight bag for filling purposes.

25. A head piece blank as in claim 24 including means at the end edge of said crown portion adaptable to be secured to a part of the said headband portion substantially 180° away from and opposed to the crown portion forward edge securement to the headband portion,
    said latter means comprising a rearward tab extension of the crown portion adapted to lie against the headband portion and be attached thereto, said rearward tab extension open through at least some portion thereof into the crown portion for filling purposes.

26. A blank as in claim 24 wherein said crown portion is divided into two elongate hollow bags of sealable liquidtight construction, each of said bags having an opening thereinto for filling purposes.

27. A blank as in claim 24 wherein said crown portion is divided centrally into two aligned, substantially equal sized, hollow bags of sealable, liquidtight construction running lengthwise substantially at right angles to the edge connection of the headband portion and crown portion, said bags open at the end edges thereof for filling purposes.

28. A head piece blank as in claim 24 including a pair of substantially triangular grasping tabs, one on each side edge of the crown portion, said tabs extending outwardly away from the crown portion side edges adjacent the connection of the headband and crown portions.

29. A head exchanging head piece for cooling or heating the entire scalp (hair bearing) area of the human head, comprising, in combination:
    an elongate, substantially rectangular headband portion adapted to be continuously and circumferentially wrapped around a human head, including the forehead, the temple-ear head side zones and the lower back portion of the cranial vault,
    said headband portion having substantially parallel, spaced apart, opposed upper and lower edges and end edges, the latter substantially at right angles to the former, as well as two free ends at the end edges thereof,
    the entire headband portion comprising but a single, continuous, elongate, rectangular hollow bag sealed continuously and circumferentially therearound at the upper, lower and end edges,
    the headband portion being sufficiently long that the end edges thereof abut and somewhat overlie one another when wrapped around a human head,
    said headband portion bag containing materials for heat exchange,
    means engageable between the free ends of said headband portion adapted to secure said free ends together, in contact with one another, to form a continuous headband, a crown portion for said head piece having a forward edge secured centrally to the substantial center of the upper edge of the headband portion, side edges extending rearwardly from the said forward edge securement and an end edge spaced rearwardly from and substantially parallel to the forward edge, said crown portion divided into two elongate, hollow bags of sealed, liquidtight construction, said bags each containing materials for heat exchange, an elongate, grasping tab portion connected to each one of the side edges of the crown portion adjacent the front edge connection thereof, means at the end edge of said crown portion adapted to secure said end edge to a part of the said headband portion substantially 180° away from and opposed to the crown portion forward edge securement to the headband portion, said latter means comprising a rearward tab extension of the crown portion adapted to lie against the free ends of the headband portion after the end edges of same have been secured to one another and be attached thereto, and means for securing the upper edge of the headband portion to the side edges of the crown portion, whereby to form, when the end edges of the headband portion are secured together, the end edge of the crown portion is secured to the headband portion and upper edge of the headband portion are secured to the side edges of the crown portion, a continuous, scalp containing head piece for completely and uniformly heat exchanging the hair bearing zone of the human scalp.

30. A head piece as in claim 29 wherein the means for securing the headband portion end edges together comprises an elongate, resilient flap having adhesive material on one side thereof, said flap overlying and adhering to portions of the outer walls of the headband portion adjacent the free ends thereof.

31. A head piece as in claim 29 wherein the heat exchanging materials in the headband portion comprise at least one water containing bag which is itself adapted to be pressure ruptured, and dry chemical adapted to react with the water on rupture of the bag to provide the heat exchanging reaction.

32. A head piece as in claim 29 wherein the heat exchanging materials in the headband portion comprise two water containing bags which are each adapted to be pressure ruptured, said bags positioned one adjacent each end edge of the headband and dry chemical adapted to react to the water on rupture of the bags to provide the heat exchanging reaction.

33. A head piece as in claim 29 wherein the crown portion is divided centrally into two aligned, substantially equal sized, elongate bags of sealed, liquidtight construction running lengthwise substantially at right angles to the forward edge connection of the headband and crown portions.

34. A head piece as in claim 29 wherein the rearward tab extension of the crown portion is adapted to overlie the said secured headband end edge portion after the end edges of the latter have been secured to one another and be attached thereto, said tab extension including an adhesive flap on each side thereof having adhesive material on one side thereof for securing said crown portion tab extension and headband portions together.

35. A head piece as in claim 29 wherein the last said means comprises at least one elongate strap connecting the upper edge of the headband portion and the adjacent side edges of the crown portion on the opposite sides of the head piece together with one another.

36. A head piece as in claim 29 wherein the heat exchanging materials in each of the two crown portion bags comprise one sealed water containing bag adapted to be pressure ruptured positioned therewithin, as well as some dry chemical material adapted to react with the water on rupture of the bag containing the water.

37. A head piece as in claim 29 wherein the heat exchanging materials in the headband portion and crown bag portion comprise a fluidic chemical substance adapted to be refrigerated for cooling purposes or heated for heating purposes.

* * * * *